United States Patent
Bergheim

(10) Patent No.: US 10,219,899 B2
(45) Date of Patent: Mar. 5, 2019

(54) CARDIAC VALVE REPLACEMENT SYSTEMS

(75) Inventor: Bjarne Bergheim, Laguna Hills, CA (US)

(73) Assignee: MEDTRONIC 3F THERAPEUTICS, INC., Irvine, CA (US)

( * ) Notice: Subject to any disclaimer, the term of this patent is extended or adjusted under 35 U.S.C. 154(b) by 1970 days.

(21) Appl. No.: 10/831,770

(22) Filed: Apr. 23, 2004

(65) Prior Publication Data

US 2005/0240200 A1 Oct. 27, 2005

(51) Int. Cl.
- *A61F 2/24* (2006.01)
- *A61B 8/00* (2006.01)
- *A61F 2/01* (2006.01)
- *A61B 8/12* (2006.01)
- *A61B 17/04* (2006.01)

(Continued)

(52) U.S. Cl.
CPC ............ *A61F 2/2427* (2013.01); *A61B 8/445* (2013.01); *A61F 2/01* (2013.01); *A61F 2/2412* (2013.01); *A61F 2/2433* (2013.01); *A61B 8/12* (2013.01); *A61B 17/04* (2013.01); *A61B 17/068* (2013.01); *A61B 17/3468* (2013.01); *A61B 2017/00243* (2013.01); *A61B 2017/00247* (2013.01); *A61B 2017/22097* (2013.01); *A61B 2018/00392* (2013.01); *A61F 2230/0006* (2013.01)

(58) Field of Classification Search
CPC .......... A61B 2017/348; A61B 1/00101; A61B 17/34; A61B 17/3468; A61F 2/2412; A61F 2/2409; A61F 2/2427
USPC ......... 606/99, 108, 192, 194, 127, 159, 200, 606/198; 623/1.11, 1.24, 1.26, 2.11, 623/2.14–2.16, 2.1, 2.12, 2.13; 604/103.1, 264, 95.03, 96.01, 103, 509, 604/907, 915, 920
See application file for complete search history.

(56) References Cited

U.S. PATENT DOCUMENTS 4,419,095 A * 12/1983 Nebergall et al. ......... 604/103.1
4,445,509 A * 5/1984 Auth ............................ 606/159

(Continued)

OTHER PUBLICATIONS

Morris, Nichols, Arsht & Tunnel llp, Letter of Jeremy A. Tigan submitted in *Endoheart AG v. Edwards Lifesciences Corporation* (C.A. No. 14-1473(LPS)(CJB)), Apr. 8, 2016.

(Continued)

*Primary Examiner* — Brian Pellegrino
(74) *Attorney, Agent, or Firm* — Medler Ferro Woodhouse & Mills PLLC

(57) ABSTRACT

Methods and systems for introducing a delivery device, having a prosthesis, in the heart at or near the apex of the heart are provided. The methods include the steps of piercing the apex of the heart with a tissue piercing end of the delivery device, advancing the prosthesis to the target site and disengaging the prosthesis from the delivery device at the target site for implantation. The valve replacement systems are configured to deliver a replacement heart valve to a target site in or near a heart. The valve replacement system includes a trocar or other suitable device to penetrate the heart at or near the apex of the heart, a delivery member that is movably disposed within the trocar, and a replacement cardiac valve disposed on the delivery member. The delivery member optionally includes mechanical or inflatable expanding members for implantating the prosthetic valve at the target site.

19 Claims, 14 Drawing Sheets

(51) Int. Cl.
  *A61B 17/068* (2006.01)
  *A61B 17/34* (2006.01)
  *A61B 17/00* (2006.01)
  *A61B 18/00* (2006.01)
  *A61B 17/22* (2006.01)

(56) References Cited

U.S. PATENT DOCUMENTS

| | | | |
|---|---|---|---|
| 5,370,685 A | 12/1994 | Stevens | |
| 5,411,552 A | 5/1995 | Andersen | |
| 5,480,424 A | 1/1996 | Cox | |
| 5,486,183 A | 6/1996 | Middleman et al. | |
| 5,571,215 A * | 11/1996 | Sterman | A61B 17/00234 623/904 |
| 5,578,076 A * | 11/1996 | Krueger et al. | 623/2.11 |
| 5,713,950 A | 2/1998 | Cox | |
| 5,749,848 A * | 5/1998 | Jang et al. | 606/198 |
| 5,824,063 A | 10/1998 | Cox | |
| 5,972,030 A | 10/1999 | Carrison | |
| 5,989,281 A | 11/1999 | Barbut et al. | |
| 6,059,719 A * | 5/2000 | Yamamoto et al. | 600/104 |
| 6,092,529 A | 7/2000 | Cox | |
| 6,267,783 B1 | 7/2001 | Letendre et al. | |
| 6,269,819 B1 | 8/2001 | Oz | |
| 6,270,526 B1 | 8/2001 | Cox | |
| 6,277,139 B1 | 8/2001 | Levinson et al. | |
| 6,425,916 B1 * | 7/2002 | Garrison et al. | 623/2.11 |
| 6,451,025 B1 | 8/2002 | Jervis | |
| 6,447,539 B1 | 9/2002 | Nelson | |
| 6,458,153 B1 | 10/2002 | Bailey | |
| 6,461,366 B1 | 10/2002 | Seguin | |
| 6,461,382 B1 | 10/2002 | Cao | |
| 6,478,806 B2 | 11/2002 | McFarlane | |
| 6,562,020 B1 | 5/2003 | Constantz | |
| 6,582,462 B1 | 6/2003 | Anderson | |
| 6,613,063 B1 | 9/2003 | Hunsberger | |
| 6,673,109 B2 | 1/2004 | Cox | |
| 6,682,559 B2 | 1/2004 | Myers | |
| 6,719,787 B2 | 4/2004 | Cox | |
| 6,719,788 B2 | 4/2004 | Cox | |
| 6,719,789 B2 | 4/2004 | Cox | |
| 6,830,585 B1 * | 12/2004 | Artof et al. | 623/2.11 |
| 6,939,359 B2 | 9/2005 | Tu | |
| 7,025,780 B2 * | 4/2006 | Gabbay | A61F 2/2436 623/2.13 |
| 8,182,530 B2 | 5/2012 | Huber | |
| 2002/0049468 A1 | 4/2002 | Streeter et al. | |
| 2002/0123786 A1 | 9/2002 | Gittings et al. | |
| 2002/0161394 A1 | 10/2002 | Macoviak et al. | |
| 2002/0173811 A1 | 11/2002 | Tu et al. | |
| 2003/0074057 A1 | 4/2003 | Rosengart | |
| 2003/0130668 A1 | 7/2003 | Nieman et al. | |
| 2003/0181843 A1 | 9/2003 | Bibber et al. | |
| 2004/0199200 A1 * | 10/2004 | Teague | A61B 17/221 606/200 |
| 2004/0220608 A1 | 11/2004 | D'Aquanni et al. | |
| 2005/0075659 A1 * | 4/2005 | Realyvasquez | A61F 2/2427 606/167 |
| 2005/0075712 A1 | 4/2005 | Biancucci | |
| 2005/0075724 A1 | 7/2005 | Svanidze | |
| 2005/0177187 A1 | 8/2005 | Gray et al. | |
| 2006/0129180 A1 | 6/2006 | Tsugita et al. | |

OTHER PUBLICATIONS

USPTO Office Action in U.S. Appl. No. 11/023,783 dated Sep. 26, 2008.
Response to Office Action and Declaration of Charles Hans Huber in U.S. Appl. No. 11/023,763 dated Mar. 26, 2009.

* cited by examiner

CARDIAC VALVE REPLACEMENT SYSTEMS

FIELD OF THE INVENTION

The present invention relates generally to methods and systems for cardiovascular surgery. More particularly, the invention relates to methods and systems for the repair, removal, and/or replacement of heart valves, and also for providing temporary valves and/or distal embolic protection during cardiovascular surgery.

BACKGROUND OF THE INVENTION

Various surgical techniques may be used to repair a diseased or damaged heart valve, such as annuloplasty (contracting the valve annulus), quadrangular resection (narrowing the valve leaflets), commissurotomy (cutting the valve commissures to separate the valve leaflets), or decalcification of valve and annulus tissue. Alternatively, the diseased heart valve may be replaced by a prosthetic valve. Where replacement of a heart valve is indicated, the dysfunctional valve is typically removed and replaced with either a mechanical or tissue valve. Tissue valves are often preferred over mechanical valves because they typically do not require long-term treatment with anticoagulants.

A number of different strategies have been used to repair or replace a defective heart valve. Open-heart valve repair or replacement surgery is a long and tedious procedure and involves a gross thoracotomy, usually in the form of a median sternotomy. In this procedure, a saw or other cutting instrument is used to cut the sternum longitudinally and the two opposing halves of the anterior or ventral portion of the rib cage are spread apart. A large opening into the thoracic cavity is thus created, through which the surgeon may directly visualize and operate upon the heart and other thoracic contents. The patient must be placed on cardiopulmonary bypass for the duration of the surgery.

Open-chest valve replacement surgery has the benefit of permitting the direct implantation of the replacement valve at its intended site. This method, however, is highly invasive and often results in significant trauma, risk of complications, as well as extended hospitalization and painful recovery period for the patient.

Minimally invasive percutaneous valve replacement procedures have emerged as an alternative to open-chest surgery. Unlike open-heart procedures, this procedure indirect and involves intravascular catheterization from a femoral artery to the heart. Because the minimally invasive approach requires only a small incision, it allows for a faster recovery for the patient with less pain and bodily trauma. This, in turn, reduces the medical costs and the overall disruption to the life of the patient.

The use of a minimally invasive approach, however, introduces new complexities to surgery. An inherent difficulty in the minimally invasive percutaneous approach is the limited space that is available within the vasculature. Unlike open heart surgery, minimally invasive heart surgery offers a surgical field that is only as large as the diameter of a blood vessel. Consequently, the introduction of tools and prosthetic devices becomes a great deal more complicated. The device must be dimensioned and configured to permit it to be introduced into the vasculature, maneuvered therethrough, and positioned at a desired location. This may involve passage through significant convolutions at some distance from the initial point of introduction.

Accordingly, while heart valve surgery produces beneficial results for many patients, numerous others who might benefit from such surgery are unable or unwilling to undergo the trauma and risks of current techniques. Therefore, what is needed are methods and devices for performing heart valve repair and replacement as well as other procedures within the heart and great vessels of the heart that provide greater ease of access to the heart valves than the current minimally invasive techniques, while at the same time reducing the trauma, risks, recovery time and pain that accompany more invasive techniques.

SUMMARY OF INVENTION

The present invention provides methods and systems for performing cardiovascular surgery, wherein access to the heart or great vessels is provided through the apical area of the heart. The apical area of the heart is generally the blunt rounded inferior extremity of the heart formed by the left and right ventricles. In normal healthy humans, it generally lies behind the fifth left intercostal space from the midsternal line.

The unique anatomical structure of the apical area permits the introduction of various surgical devices and tools into the heart without significant disruption of the natural mechanical and electrical heart function. Because the methods and systems of this invention permit direct access to the heart and great vessels through the apex, it is not limited by the size constraints which are presented by percutaneous surgical methods. While access to the heart through the femoral vessels in percutaneous methods are limited to the diameter of the vessel (approximately 8 mm), access to the heart through the apical area is significantly larger (approximately 25 mm). Thus, apical access to the heart permits greater flexibility with respect to the types of devices and surgical methods that may be performed in the heart and great vessels.

Accordingly, it is one object of this invention to provide methods and devices for the repair, removal, and/or replacement of heart valves by access through the apical area of the heart.

In one preferred embodiment of the present invention, a method for delivering a prosthesis to a target site in or near a heart is provided. The method comprises introducing a delivery device in the heart at or near the apex of the heart, wherein the delivery device includes a prosthesis, advancing the prosthesis to the target site, and disengaging the prosthesis from the delivery device at the target site for implantation.

The present invention also provides valve replacement systems for delivering a replacement heart valve to a target site in or near a heart. In one embodiment, the valve replacement system comprises a trocar or other suitable device to penetrate the heart at or near the apex of the heart, a delivery member that is movably disposed within the trocar, and a replacement cardiac valve disposed on the delivery member.

The valve replacement system may be used to deliver a variety of prosthetic heart valves, including stented and stentless tissue valves. In another embodiment of the present invention, the delivery member may further comprise mechanical or inflatable expanding members to facilitate implantation of the prosthetic valve at the target site.

In another embodiment of the present invention, an imaging system may be provided to view the operating field. The imaging system may be used at any time or throughout the duration of the surgery. Imaging systems are well-known to one of skill in the art and include transesophageal echo, transthoracic echo, intravascular ultrasound imaging (IVUS), or an injectable dye that is radiopaque. Cinefluoroscopy may also be utilized.

In one embodiment, the imaging system is deliverable through a catheter or cannula to the operating field. In another embodiment of the present invention, an ultrasound transducer may be located on the delivery member at one or both sides of the expandable balloon. In yet another embodiment of the present invention, the ultrasound transducer may be located on the balloon of the delivery member.

In yet another embodiment of the present invention, the method and system may further comprise means to remove at least a portion of the patient's heart valve by a cutting tool that is disposed on the delivery member. The cutting tool may be made of an electrically conductive metal that provides radiofrequency energy to the cutting tool for enhanced valve removal. The high frequency energy ablation is well known in the art.

In a further embodiment of the present invention, the methods and devices of the present invention may be adapted to provide a valve decalcification system, wherein the delivery member is capable of providing the dissolution solution to the treatment site by access through the apical area of the heart. The delivery member may be a catheter that is configured with means to both introduce and remove the dissolution solution to the treatment site. The delivery member may also provide means for isolating the treatment site to prevent the dissolution solution from entering into the patient's circulatory system. Such means for isolating the treatment site may include a barrier, such as a dual balloon system on the catheter that inflate on both sides of the treatment site.

The present invention also provides for devices and methods for providing distal embolic protection. More particularly, the invention provides a filter for trapping embolic material while concurrently providing a temporary valve in the same device. The presence of a valve in a filter assembly prevents flush back of embolic material and debris, while still allowing fluid flow into the filter during surgery. The valve-filter combination may be compressed and expanded to allow entry into small blood vessels or other body cavities. In one embodiment of the present invention, a valve-filter assembly is implanted in the heart or great vessel of the heart, downstream from the surgical site.

The above aspects and other objects, features and advantages of the present invention will become apparent to those skilled in the art from the following description of the preferred embodiments taken together with the accompanying figures.

DESCRIPTION OF THE PREFERRED EMBODIMENTS

FIGS. 1 through 13 show an embodiment of the method and systems for the repair, removal, and/or replacement of heart valves, and also for providing distal embolic protection and a temporary valve during cardiovascular surgery.

Valve Replacement Method and System

Figure 1:
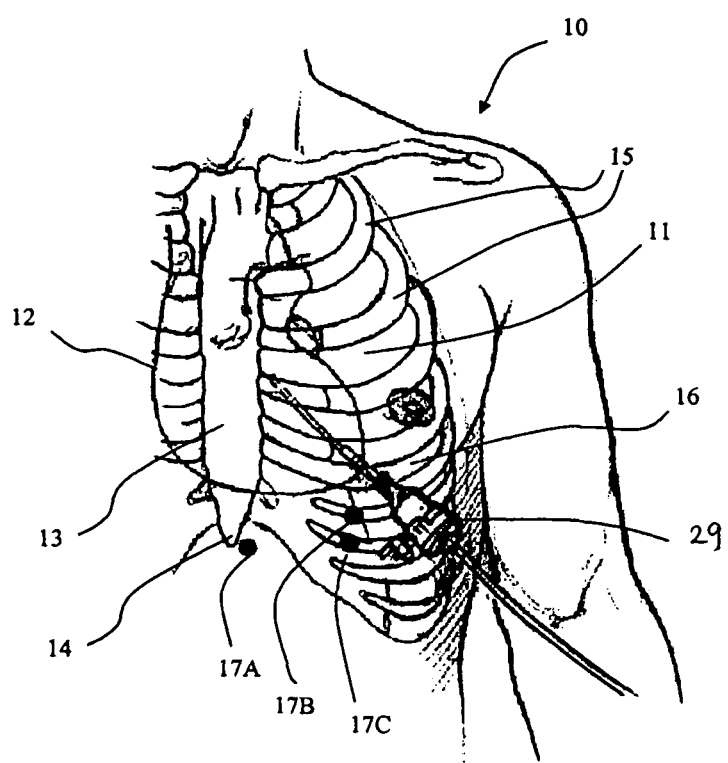
FIG. 1 is a partial front view of a patient's chest showing a replacement valve delivery device introduced into the apex of the heart through the fifth intercostal space.

FIG. 1 is a partial front view of the chest (11) of a patient (10) and shows the position of the valve replacement system (29) in relation to other anatomical landmarks, such as the sternum (13), xiphoid (14), ribs (15), and heart (12). The valve replacement system (29) is depicted as entering the body cavity through the fifth intercostal space (16) and through the apex of the heart (12). The valve replacement system (29) may enter the body cavity through various other locations (17A, 17B and 17C) in the chest (11).

In one preferred embodiment of the present invention, the valve replacement system comprises a trocar or other suitable device for penetrating the apical area of the heart and a delivery member and a replacement prosthetic valve disposed on the delivery member.

The methods and systems of the present invention may be used to implant a variety of prosthetic heart valve assemblies known in the art, including stented and stentless tissue valves. Stented valves may be expandable by mechanical or balloon expansion devices, or they may be self-expanding. Self-expanding stents may be constructed from metal alloys, such as Nitinol, described in U.S. Pat. No. 6,451,025, incorporated herein by reference.

Alternatively, the methods and devices of the present invention may also be used to implant a stentless prosthetic heart valve. In one embodiment of the present invention, the delivery member is adapted to position the tissue valve at the target site and the deliver member further comprises a means to suture or staple the tissue valve to the valve annulus.

Examples of suitable prosthetic valves are disclosed in the following commonly owned patents: U.S. Pat. Nos. 6,682,559; 5,480,424; 5,713,950; 5,824,063; 6,092,529; 6,270,526; 6,673,109; 6,719,787; 6,719,788; and 6,719,789, incorporated herein by reference. Examples of other valve assemblies suitable for use in connection with the present invention are described in U.S. Pat. Nos. 5,411,552; 6,458,153; 6,461,382; and 6,582,462, incorporated herein by reference.

Figure 2:
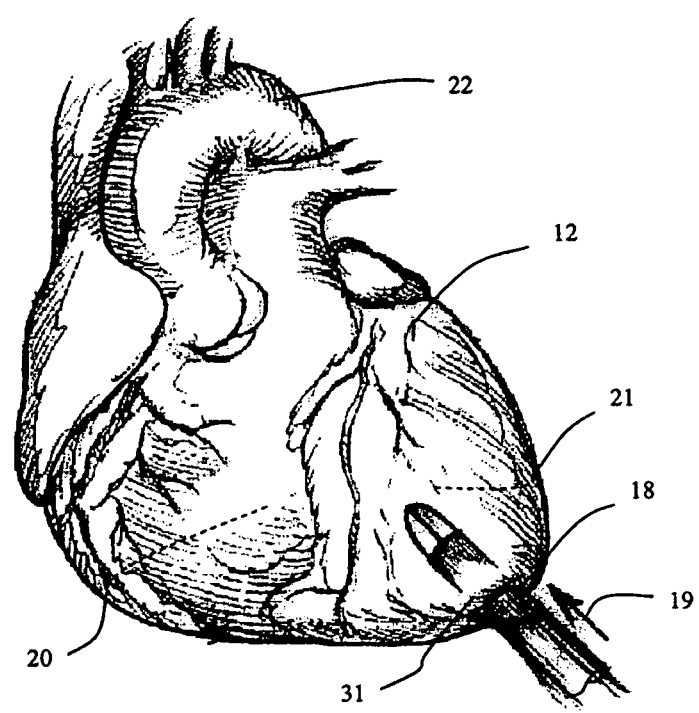
FIG. 2 depicts a trocar of the replacement valve delivery device penetrating the apex of the heart and into the left ventricle.

Trocars suitable for use in connection with the present invention typically comprise a hollow lumen and a first and second ends. The first end comprises a means for penetrating the heart tissue and the second end comprises a port through which the delivery member may be introduced into the hollow lumen of the trocar and into the heart. FIG. 2 depicts a trocar penetrating through the apex (18) of the heart (12). The moving direction of the trocar (31) is indicated by the arrow (19). The trocar (31) can enter either the right ventricle (20) or the left ventricle (21). To access the aortic or mitral valve, the trocar (31) would preferably pass through the left ventricle (21). This yields direct access to the aortic or mitral valve. To access the pulmonary or tricuspid valve, the trocar (31) would preferably pass through the right ventricle (20).

In another embodiment of the present invention, the trocar further comprises a valve disposed within the lumen. The valve is designed to reduce significant backflow of blood out of the heart after the trocar is inserted into the beating heart, while at the same time permitting the introduction of the delivery member and other surgical devices in through the trocar. Other suitable trocars and devices are well known in the art and are disclosed in U.S. Pat. Nos. 5,972,030; 6,269,819; 6,461,366; 6,478,806; and 6,613,063, incorporated herein by reference.

Figure 14:
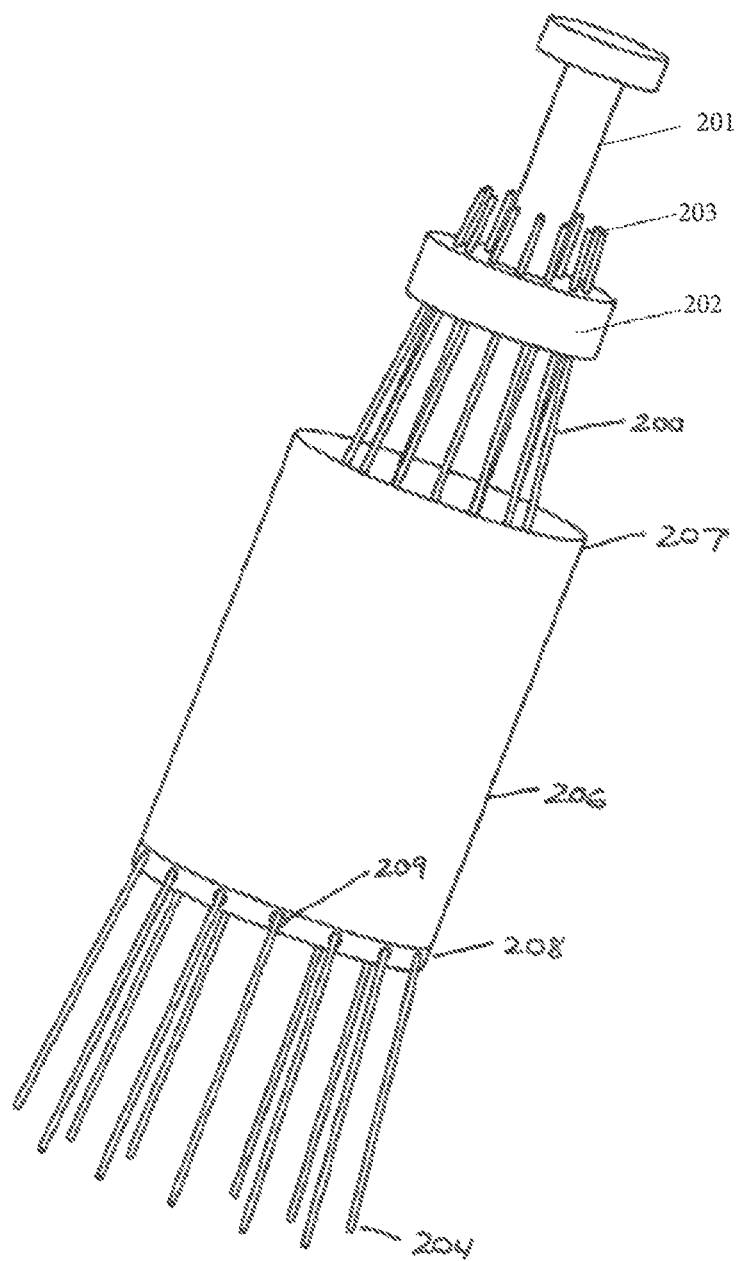
FIG. 14 shows a perspective view of a mechanical expansion and contracting device for use in embodiments hereof.

The delivery member of the valve replacement system is adapted to deliver the prosthetic valve to the site of implantation, through the apical area of the heart. In one embodiment of the present invention, the delivery member is a rod comprising a mechanical expansion and contracting device. In one embodiment of the present invention shown in FIG. 14, the mechanical expansion and contracting device may comprise a plurality of hollow wires (200) in a circular arrangement, a circular element (202) that holds the wires (200) together at their proximal ends (203), a grip handle (201), and a cylinder (206) comprising outwardly angled holes (209) along its perimeter, the cylinder (206) having a proximal end (207) and a distal end (208). The prosthetic valve is disposed around the mechanical expansion members in a contracted state and delivered to the target site for implantation. Once properly positioned, the mechanical expansion members are expanded by pushing the wires (200) through the angled holes (209) and the prosthetic valve is expanded for implantation. More particularly, the holes (209) in the cylinder (206) are preferably drilled at an outward angle so that by forcing the wires (200) through the angled holes (209), the distal ends (204) of the wires (200) are driven radially outward. As the wires (200) are pushed further through the outwardly angled cylinder holes (209), the further the wires (200) spread radially, thereby expanding the prosthetic valve that is positioned over the wires (200). Accordingly, the angle of the cylinder holes (209) controls the relationship between the longitudinal movement of the wires (200) and their radial dilation.

In another embodiment of the present invention, the mechanical expansion and contracting device for implanting the prosthetic valve assembly may include a hollow tube surrounded by a plurality of wall panels connected to a plurality of spring loaded pins extending from the exterior of the tube to a central plate at the interior of the tube. The central plate has spiral shaped edges, such that rotation of the central plate pushes the pins radially outward. Other mechanical expansion and contracting devices are more fully described in co-pending U.S. patent application Ser. No. 10/680,719.

Figure 3:
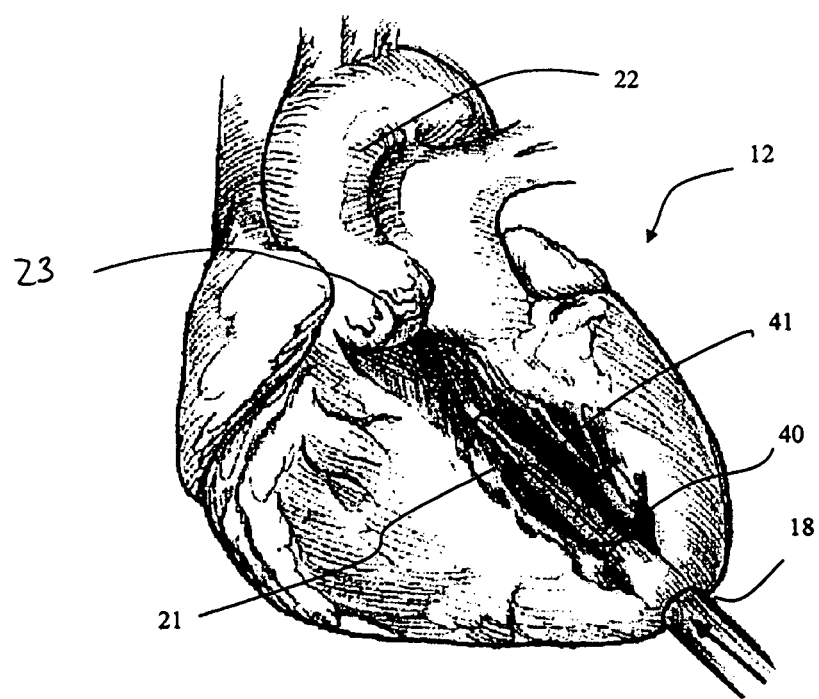
FIG. 3 shows a balloon expandable delivery member being introduced into the left ventricle through trocar positioned at the apex of the heart.

In yet another embodiment of the present invention, the delivery member may be a hollow tube having an expandable member, such as a balloon. FIG. 3 depicts a delivery member (40) having a balloon (41) being inserted through the apex (18) and into the left ventricle (21) and advancing towards the native aortic valve (23) of the heart (12). Once the balloon (41) is placed within the aortic valve (23), it may be inflated to widen a stiff or narrowed heart valve (stenotic heart valve) and improving blood flow through the heart and to the rest of the body. This allows the heart to pump more effectively and reduces pressures in the heart and lungs. Previous methods for performing valvuloplasty required the insertion of a catheter at the femoral artery, which is then guided through the heart and positioned through the diseased heart valve. The methods and devices of this present invention, however, provide a more direct route to the valve to be treated.

Figure 4:
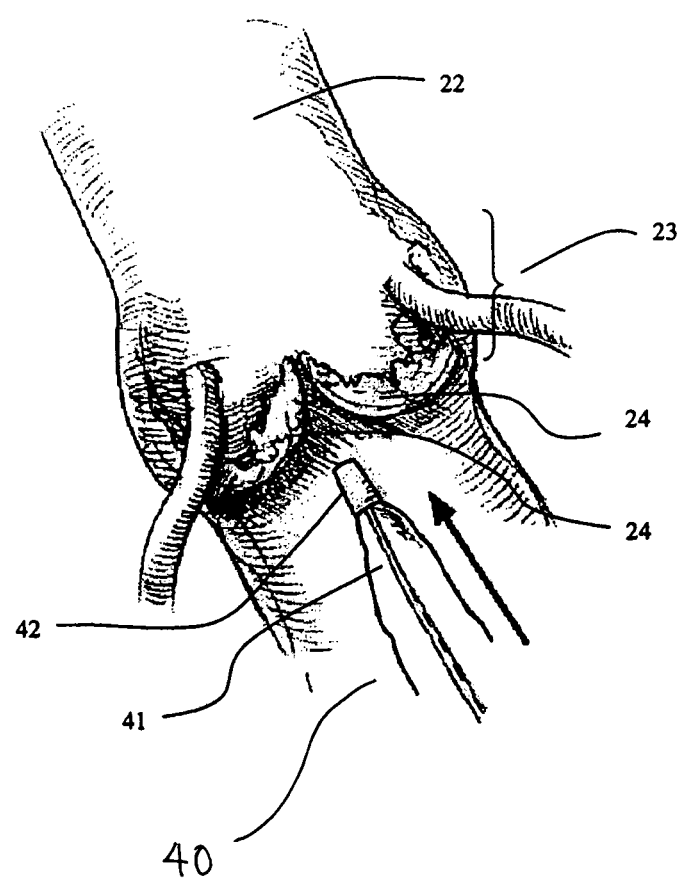
FIG. 4 depicts a balloon expandable member being advanced toward the aortic valve.

FIG. 4 shows a close-up view of the delivery member (40) and balloon (41) advancing toward the aortic valve (23) where aortic stenosis is evident. As depicted here, the aortic valve has a plurality of valve leaflets (24). In one embodiment, the delivery member (40) comprises a tip or distal attachment (42) adapted to receive a variety of auxiliary devices to assist in the valve replacement procedure. Such auxiliary devices may include a distal embolic protection assembly, a temporary valve, an imaging system, a valve removal system, a valve decalcification system.

Figure 5:
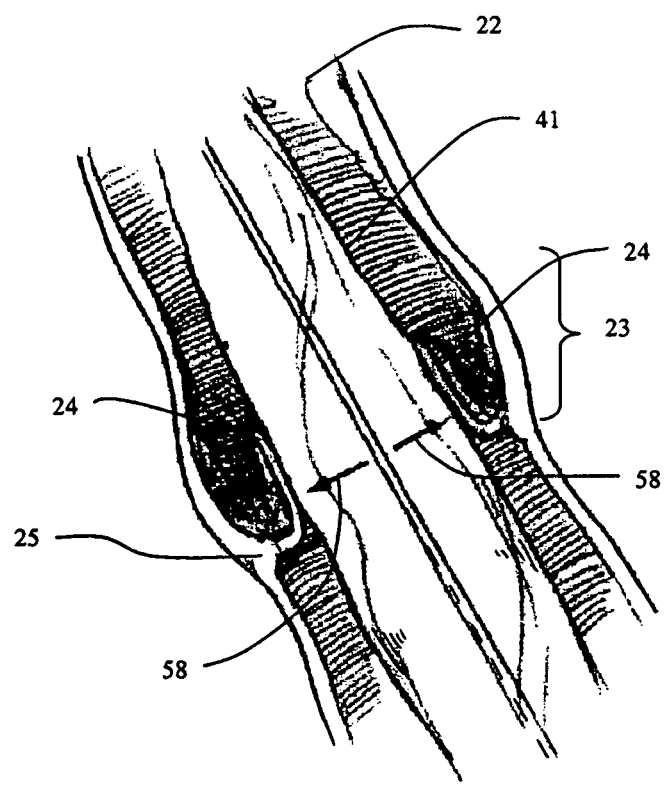
FIG. 5 shows the placement of the balloon expandable member within a stenotic aortic valve.
Figure 6:
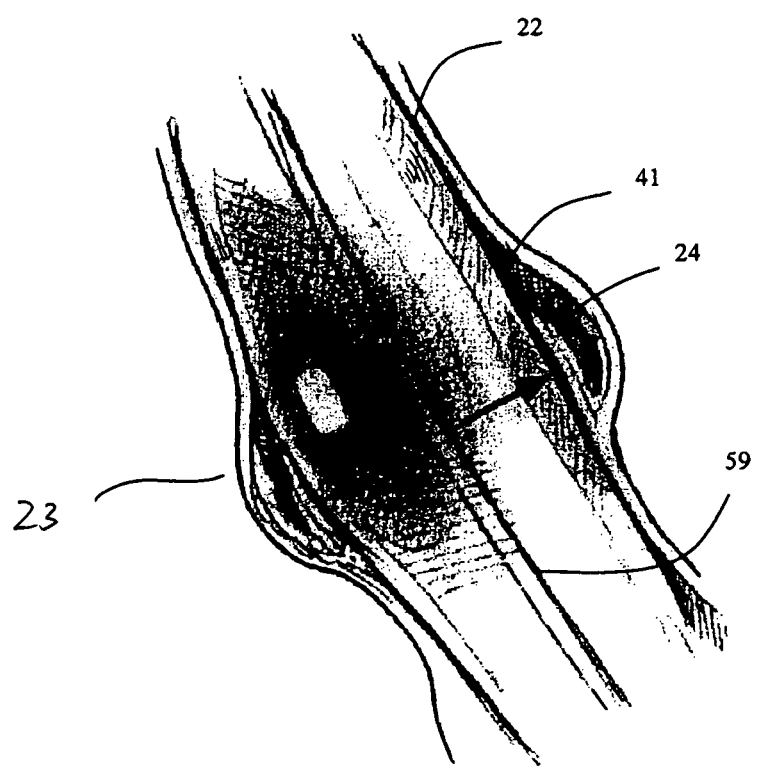
FIG. 6 shows the expanded balloon expandable member within a stenotic aortic valve.

FIG. 5 shows a balloon (41) positioned in the aorta (22) and within the aortic valve (23) and aortic valve annulus (25). The balloon (41) is depicted as inflating in a radial direction as indicated by the arrows (58) to compress the valvular leaflets (24) against walls of the aorta (22). In FIG. 6, the balloon (41) is fully inflated to widen a stenotic aortic valve (23) by pressing the leaflets (24) against the aortic valls. An inner element (59) may also be used for inserting a guidewire for controlling tip deflection or a fluid infusion conduit for balloon inflation.

Figure 7:
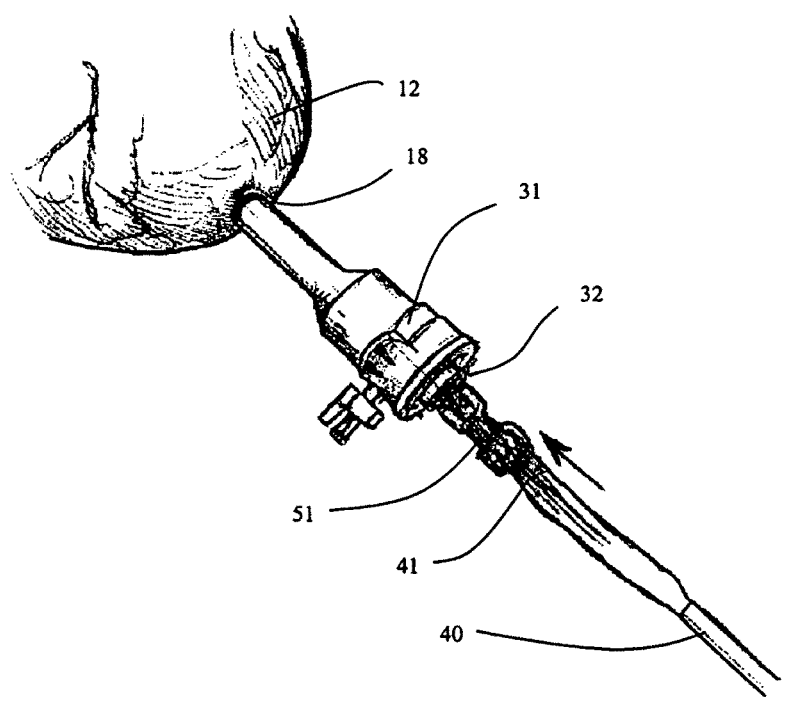
FIG. 7 shows the insertion of a replacement valve delivery member having a prosthetic replacement valve disposed around a balloon expandable member through the apex of the heart.

FIG. 7 shows the insertion of the delivery member (40) having a balloon expansion member (41). A collapsed replacement prosthetic valve (51) is disposed on the balloon expansion member (41) and is introduced into the port (32) of the trocar (31). The delivery member (40) is depicted as passing through the apex (18) of the heart (12).

Figure 8:
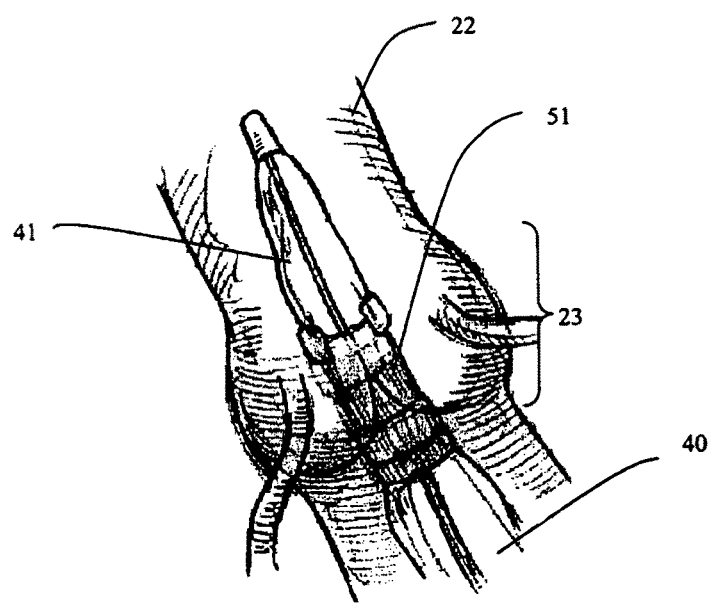
FIG. 8 is a cross-sectional view of the replacement valve delivery member positioned within the aorta.
Figure 9:
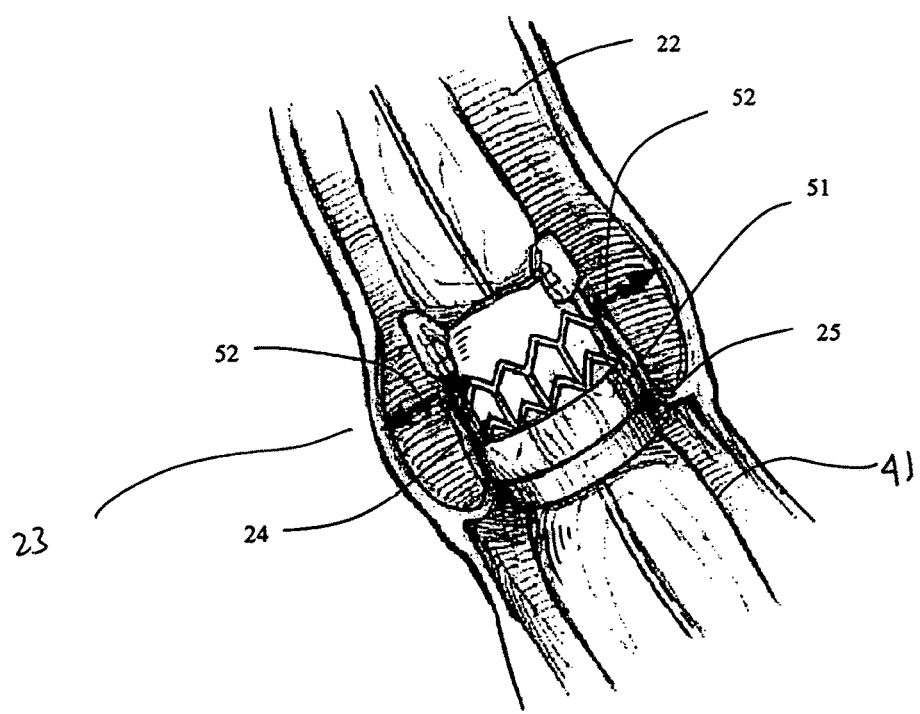
FIG. 9 depicts the expansion of the prosthetic replacement valve by the balloon of the replacement valve delivery member.

FIGS. 8-9 show expansion of the balloon (41) positioned within the native aortic valve (23). FIG. 8 is a cross-sectional view of the replacement valve delivery member (40) comprising a balloon (41) and a replacement valve (51) disposed on an unexpanded balloon (41). The replacement valve (51) is depicted here as being positioned within the aortic valve (23). FIG. 9 depicts the radial expansion (52) of the balloon (41) causing the replacement valve (51) to press against the aortic valve leaflets (24) of the aortic valve (23) against the annulus (25).

Figure 10:
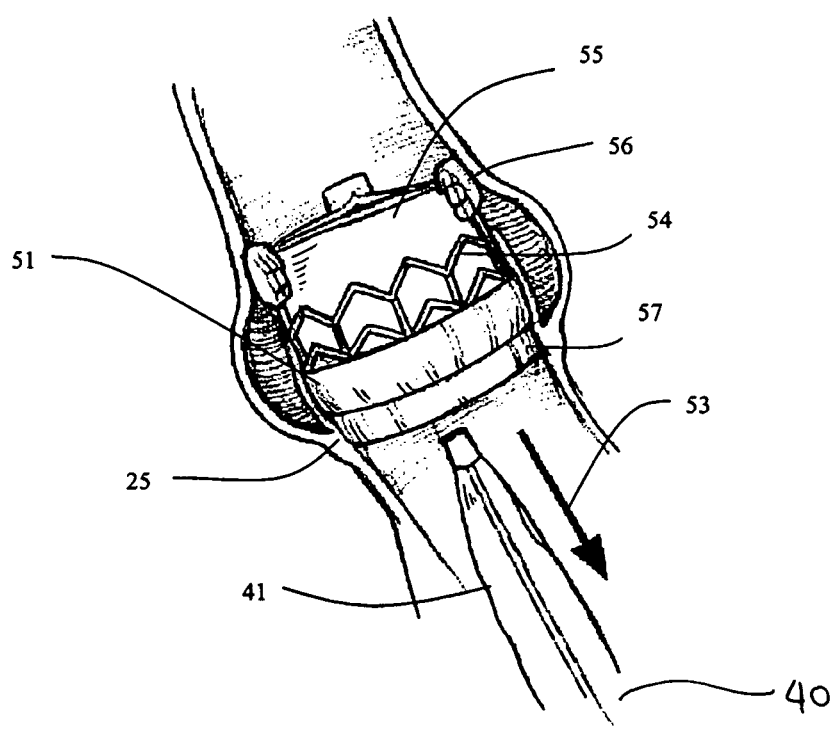
FIG. 10 shows a fully-expanded and deployed prosthetic replacement valve and a disengaged replacement valve delivery member.
Figure 11:
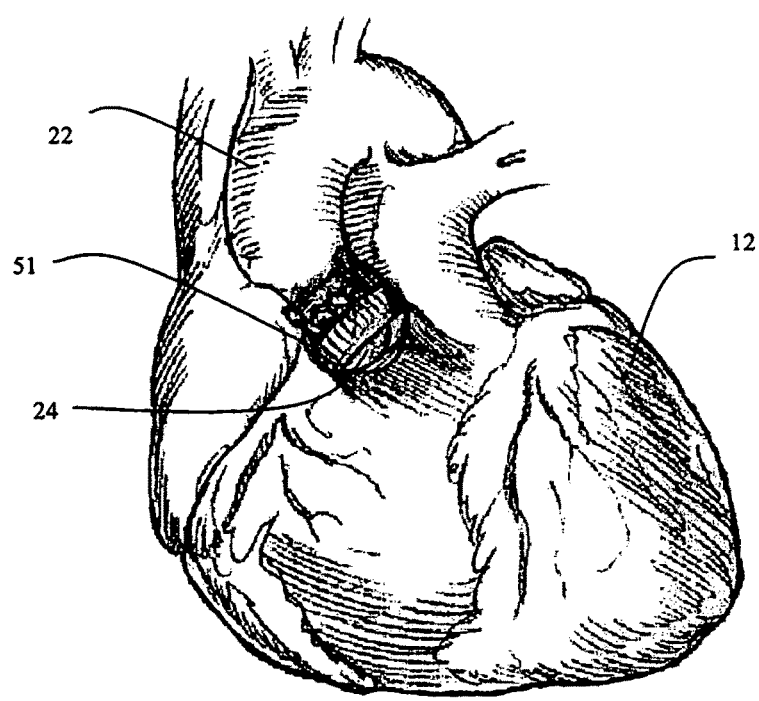
FIG. 11 is a partial cross-sectional view of the heart showing the prosthetic replacement valve positioned at the aorta.

FIG. 10 shows the deployed valve in its fully expanded state. The replacement prosthetic valve (51), as depicted here, comprises a base ring (57) and a support structure or stent (54) with tabs (56) to support the tissue valve (55). Once the prosthetic valve (51) is implanted, the balloon (41) is then deflated and the delivery member (40) is withdrawn from the body in the direction indicated by the arrow (53). FIG. 11 shows the implanted replacement valve (51) positioned in the aortic valve position.

Imaging Systems

An imaging system to view the operating field may be used at any time or throughout the duration of the surgery. Imaging systems are well-known to one of skill in the art and include transesophageal echo, transthoracic echo, intravascular ultrasound imaging (IVUS), or an injectable dye that is radiopaque. Cinefluoroscopy may also be utilized. In one embodiment, the imaging system is deliverable through a catheter or cannula to the operating field.

Intravascular ultrasound (IVUS) uses high-frequency sound waves that are sent with a device called a transducer. The transducer may be coupled to the delivery member of the present invention. In this arrangement, the sound waves bounce off of the walls of the vessel or heart and return to the transducer as echoes.

Figure 12:
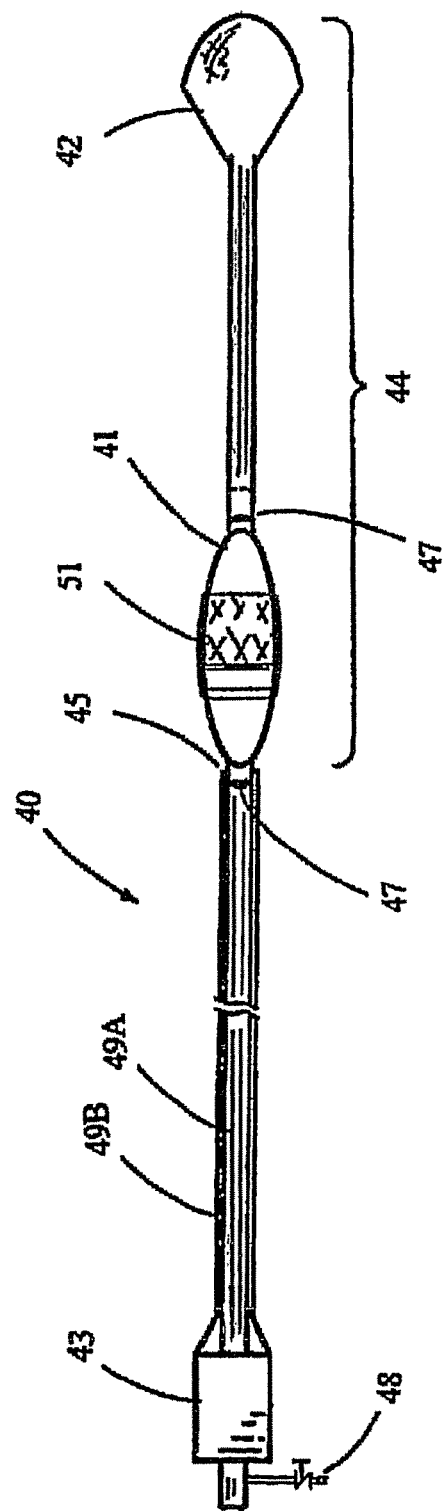
FIG. 12 shows one embodiment of the delivery member for use in a valve replacement system.

In one embodiment of the present invention, a delivery member may include at least one ultrasound transducer to provide an image of the target site before, during, and after valve implantation. FIG. 12 shows another embodiment of the delivery member of present invention. In this embodiment, the delivery member comprises an inner member (49A) that is retractable within the lumen of an outer member (49B). Upon deployment of the delivery member (40), the distal end (44) of the inner member (49A) is exposed past the end (45) of the outer member (49B).

The distal end (44) of the inner member comprises an expandable balloon (41) in fluid communication with the fluid infusion mechanism (48) and the handle (43) of the delivery member, by which the balloon (41) may be either inflated or deflated. The inner member (49A) of the delivery member (40) further comprises ultrasound transducers (47) adjacent to the expandable balloon (41) and a tip or distal attachment (42) which is adapted to receive a variety of auxiliary devices to assist in the valve replacement procedure. The auxiliary devices may be detachably coupled to the distal attachment (42) such that the auxiliary attachment devices may be released from the distal attachment member. Such auxiliary devices may include a distal embolic protection assembly, a temporary valve, an imaging system, a valve removal system, or a valve decalcification system.

While ultrasound transducers disclosed here are located adjacent to the balloon, it is appreciated that the ultrasound transducer may be placed at any location on the delivery member, on the balloon, and/or on the tip or distal attachment.

Valve Removal Systems

The present invention also provides a method or system for removing the valve with a valve removal device by access through the apical area of the heart. By way of example, the valve removal may be accomplished as taught in co-pending U.S. patent application Ser. Nos. 10/375,718 and 10/680,562, which are incorporated herein by reference as if set forth in its entirety.

In one embodiment of the present invention, the method may further comprise the step of removing at least a portion of the patient's heart valve by means of a cutting tool that is disposed on the delivery member. In another aspect of the present invention, the cutting tool may be made of an electrically conductive metal that provides radiofrequency energy to the cutting tool for enhanced valve removal. The high frequency energy ablation is well known in the art.

In another embodiment of the present invention, the delivery member includes cutting means comprising a plurality of jaw elements, each jaw element having a sharp end enabling the jaw element to cut through at least a portion of the native valve. In another aspect, the cutting means comprises a plurality of electrode elements, wherein radiofrequency energy is delivered to each electrode element, enabling the electrode element to cut through at least a portion of the native valve. In a further aspect of the present invention, the cutting means comprises a plurality of ultrasound transducer elements, wherein ultrasound energy is delivered to each transducer element enabling the transducer element to cut through at least a portion of the native valve.

Valve Decalcification Systems

The formation of atherosclerotic plaques and lesions on cardiovascular tissue, such as blood vessels and heart valves, is a major component of cardiovascular disease. A variety of different methods have been developed to treat cardiovascular diseases which are associated with calcified atherosclerotic plaques and lesions. Such methods include mechanical removal or reduction of the lesion, such as bypass surgery, balloon angioplasty, mechanical debridement, atherectomy, and valve replacement.

Calcified atherosclerotic plaques and lesions may also be treated by chemical means which may be delivered to the affected area by various catheter devices. For example, U.S. Pat. No. 6,562,020 to Constantz et al. discloses the treatment of vascular calcified lesions by using an acidic dissolution solution and a catheter fluid delivery system capable of localized flushing a vascular site. Suitable catheter devices include those described in U.S. Pat. No. 6,562,020, which is incorporated herein by reference as if set forth in its entirety.

Accordingly, in another embodiment of the present invention, the methods and devices of the present invention may be adapted to provide a valve decalcification system, wherein the delivery member is capable of providing the dissolution solution to the treatment site by access through the apical area of the heart. Suitable dissolution solutions are known in the art and are generally characterized as those which are capable of increasing the proton concentration at the treatment site to a desired level sufficient to at least partially dissolve the mineral component of a calcified atherosclerotic lesion.

The delivery member may be a catheter that is configured with means to both introduce and remove the dissolution solution to the treatment site. The delivery member may also provide means for isolating the treatment site to prevent the dissolution solution from entering into the patient's circulatory system. Such means for isolating the treatment site may include a barrier, such as a dual balloon system on the catheter that inflate on both sides of the treatment site.

Temporary Valve

During valve replacement surgery, the function of the native valve being replaced is halted and the natural fluid flow blood in the heart is therefore disrupted. This, in turn, may result in significant backflow blood pressure in the heart and vessels. There is therefore a need to prevent or reduce the backflow blood pressure that results when the natural valve function is halted during replacement valve surgery.

The present invention provides a means of providing a temporary valve either before or concomitantly with the delivery of a replacement heart valve.

In one embodiment of the present invention, the delivery member comprises a temporary valve, which may be deployed at a desired location in a collapsed state, expanded and secured to the walls of a heart or blood vessel, and then re-collapsed and removed from the body after completion of the valve replacement surgery. The temporary valve may be provided as a tip attachment to a deliver member comprising the replacement valve. Alternatively, the temporary valve may be disposed on a separate delivery member in a manner similar to the replacement heart valve.

In a preferred embodiment of the present invention, the temporary valve is deployed at a location that is sufficiently close to the non-functioning valve. The location of the temporary valve may be placed either upstream or downstream of the non-functioning valve.

Distal Embolic Protection Assemblies

In valve repair or replacement surgery, manipulation of the heavily calcified valves may result in dislodgment of calcium and valve or other surrounding tissue, with subsequent embolization and blockage. Although atheromatous debris most frequently embolizes in the brain, other affected body sites include the spleen, kidney, pancreas, and gastrointestinal tract. Embolization and blockage to these peripheral organs can lead to tissue ischemia or death. A need therefore exists for safely containing embolic material during cardiovascular surgery.

Figure 13:
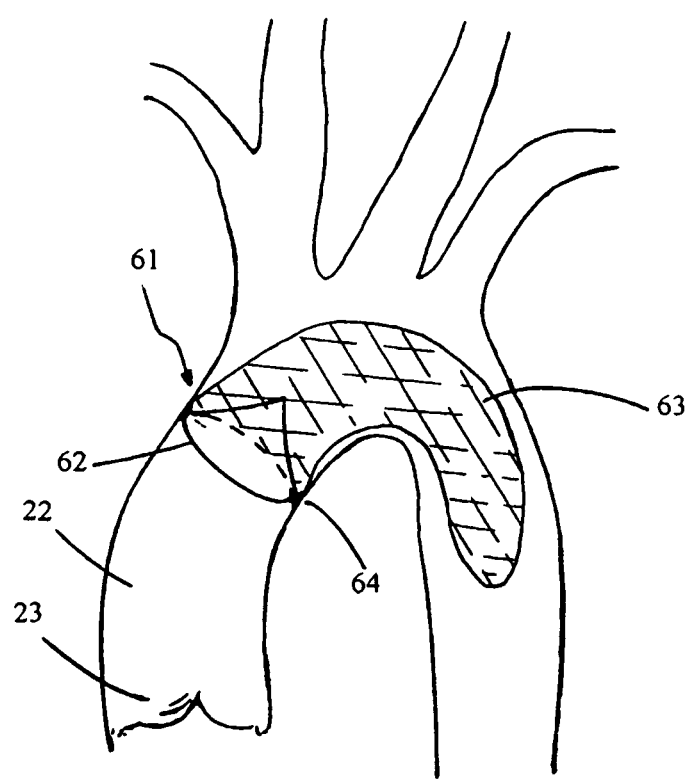
FIG. 13 shows one embodiment of a valve-filter assembly, positioned in the aorta, downstream of the aortic valve.

In one embodiment of the present invention, a valve-filter assembly is provided. This valve-filter assembly may be implanted downstream from the site before surgery is to be performed. A preferred embodiment of the valve-filter assembly is depicted in FIG. 13, which shows a valve-filter assembly (61) positioned in the aorta (22) and downstream of the aortic valve (23). The temporary valve-filter assembly (61) is comprised of a temporary valve (62) and a filter (63) extending therefrom. The valve-filter assembly provides distal embolic protection and may be delivered by a catheter or cannula or any conventional method to the downstream side of the native aortic valve (23). After the temporary valve-filter assembly is positioned at a desired location (64), it is deployed to serve the dual functions of a temporary check valve and a filter to capture any loose emboli or debris during surgery.

A valve is included in the distal embolic protection assembly to provide the dual function of acting as a temporary valve during valve replacement surgery and preventing embolic material from escaping out from the filter. Adding a one-way valve at the inflow of a filter prevents embolic material from escaping, thus reducing the incidence of embolization and blockage. A valve would concurrently provide a temporary valve for use during valve surgery. Combining both a filter and a valve in the same arrangement also creates a more compact device allowing more space for conducting other procedures. In aortic repair and replacement surgeries, for example, there is limited space in between the aortic valve and the innominate branch. Combining a filter and a valve in a compact device allows more space for devices used for the valve repair or replacement procedure.

A difficulty inherent in the percutaneous implantation of valve-filter devices, as described above, is the limited amount of space that is available within the vasculature. The device must be dimensioned and configured to permit it to be introduced into the vasculature, maneuvered therethrough and positioned downstream of the treatment site. This may involve passage through significant convolutions at some distance from the initial point of introduction. Once in position, the device must be deployable to a sufficiently large cross-section to effectively strain substantially all of the blood passing therethrough without unacceptably reducing its flow rate. Additionally, the use or the presence of such device must not interfere with the treatment of the vasculature site, nor may the treating device interfere with the function of the embolic capture device.

Moreover, it is crucial that material captured by the filters described above are contained and not allowed to leave the proximity of the filter. In valve repair surgery, for example, it is important that material dislodged during surgery and trapped by a filter placed in between the aortic valve and innominate branch is not allowed to leave the filter during back flow and hence enter the coronaries. Preventing debris from leaving the filter is especially important when larger particles are present that does not easily attach to the filter material.

The filter of the valve-filter assembly may be a mesh of any size and shape required to trap all of the embolic material while still providing sufficient surface area for providing satisfactory blood flow during use. The filter may be a sheet or bag of different mesh sizes. In a preferred embodiment, the mesh size is optimized taking into consideration such factors as flow conditions, application site, size of filter bag, and rate of clotting.

Although the invention has been described with reference to preferred embodiments and specific examples, those of ordinary skill in the art will readily appreciate that many modifications and adaptations of the invention are possible without departure from the spirit and scope of the invention as claimed hereinafter.

What is claimed:

1. A valve replacement system comprising:
   a stent-less cardiac prosthetic tissue valve comprising an outflow end and an inflow end, the prosthetic tissue valve having an expanded state when deployed and an unexpanded state during delivery;
   a delivery member configured to deliver the prosthetic tissue valve to a target site through an apex of a heart, and comprising a mechanical expansion device arranged at a distal end of the delivery member, wherein the mechanical expansion device comprises a plurality of wires in a circular arrangement and a hollow cylinder having outwardly angled holes around a perimeter thereof that are formed through a sidewall of the hollow cylinder, wherein the plurality of wires are slidably disposed through the outwardly angled holes such that the plurality of wires pass from an interior to an exterior of the hollow cylinder, the prosthetic tissue valve being releasably coupled in the unexpanded state to the hollow cylinder of the mechanical expansion device by the plurality of wires, wherein the mechanical expansion device is configured to expand the prosthetic tissue valve by distally advancing the wires through the outwardly angled holes of the hollow cylinder; and
   a trocar having a proximal end, a distal end, and a lumen extending between the proximal end and the distal end, the trocar being configured to be inserted through an intercostal space between adjacent ribs and through the heart at or near the apex of the heart such that the proximal end is positioned outside a patient body and the distal end is positioned in a ventricle of the heart, the lumen being configured to pass the prosthetic tissue valve releasably coupled in the unexpanded state to the mechanical expansion device.

2. The system of claim 1, wherein the trocar comprises a stop-valve disposed within the lumen.

3. The system of claim 1, wherein the delivery member further comprises a first ultrasound transducer configured to provide an image of the target site.

4. The system of claim 3, wherein the delivery member further comprises a second ultrasound transducer configured to provide the image of the target site.

5. The system of claim 1, wherein the delivery member further comprises a cutting means for cutting through at least a portion of a native valve, the cutting mean being attached at the distal end of the delivery member.

6. The system of claim 1, wherein the prosthetic tissue valve is configured to be implanted in the expanded state at a valve annulus of a native valve at the target site.

7. The system of claim 1, wherein the mechanical expansion device further comprises a circular element that holds the plurality of wires together at their proximal ends in the circular arrangement.

8. The system of claim 7, wherein the mechanical expansion device further comprises a grip handle attached to and extending proximally from the circular element.

9. The system of claim 7, wherein the hollow cylinder and the circular element are not attached to each other and are coupled to each other only by the plurality of wires extending therebetween.

10. A valve replacement system comprising:
a tube having a first end defining a port, a second end, and a lumen extending between the first and second ends, the tube being configured to pass through an apical area of the heart such that such that the first end is positioned outside a patient body and the second end is positioned in a ventricle of the heart;
a stent-less cardiac prosthetic tissue valve comprising an outflow end and an inflow end, the prosthetic tissue valve having an expanded state when deployed and an unexpanded state during delivery; and
a delivery member configured to deliver the prosthetic tissue valve releasably mounted in the unexpanded state thereto, wherein the delivery member comprises a plurality of wires in a circular arrangement and a hollow cylinder having outwardly angled holes around a perimeter thereof that are formed through a sidewall of the hollow cylinder, wherein the plurality of wires are slidably disposed through the outwardly angled holes such that the plurality of wires pass from an interior to an exterior of the hollow cylinder, wherein the prosthetic tissue valve is releasably mounted in the unexpanded state to the hollow cylinder of the delivery member by the plurality of wires, wherein the delivery member is configured to expand the prosthetic tissue valve by distally advancing the wires through the outwardly angled holes of the hollow cylinder, the delivery member being insertable through the port of the tube and slidable within the lumen.

11. The system of claim 10, wherein the tube further comprises a valve disposed within the lumen structured to reduce backflow of blood out of the heart after the tube has passed through the apical area of the heart.

12. The system of claim 10, further comprising valve attachment means operably coupled to the delivery member and structured to attach the stent-less cardiac prosthetic tissue valve to a valve annulus.

13. The system of claim 12, wherein the valve attachment means comprises means to staple the stent-less cardiac prosthetic tissue valve to the valve annulus.

14. The system of claim 10, wherein the delivery member further comprises a circular element that holds the plurality of wires together at their proximal ends in the circular arrangement.

15. The system of claim 14, wherein the delivery member further comprises a grip handle attached to and extending proximally from the circular element.

16. The system of claim 14, wherein the hollow cylinder and the circular element are not attached to each other and are coupled to each other only by the plurality of wires extending therebetween.

17. A valve replacement system comprising:
a tube having a first end defining a port, a second end, and a lumen extending between the first and second ends, the tube being configured to pass through an apical area of the heart such that such that the first end is positioned outside a patient body and the second end is positioned in a ventricle of the heart;
a stent-less cardiac prosthetic tissue valve comprising an outflow end and an inflow end, the prosthetic tissue valve having an expanded state when deployed and an unexpanded state during delivery; and
a delivery member configured to deliver the prosthetic tissue valve to a target site through an apex of a heart, and comprising a mechanical expansion device arranged at a distal end of the delivery member, wherein the mechanical expansion device comprises a plurality of wires, a circular element that holds the plurality of wires together at their proximal ends in a circular arrangement, and a hollow cylinder having outwardly angled holes around a perimeter thereof that are formed through a sidewall of the hollow cylinder, wherein the hollow cylinder and the circular element are not attached to each other and are coupled to each other only by the plurality of wires extending therebetween and wherein the plurality of wires are slidably disposed through the outwardly angled holes such that the plurality of wires pass from an interior to an exterior of the hollow cylinder, and
wherein the prosthetic tissue valve is releasably mounted in the unexpanded state to the hollow cylinder of the delivery member by the plurality of wires and the delivery member is configured to expand the prosthetic tissue valve by distally advancing the wires through the outwardly angled holes of the hollow cylinder, the delivery member being insertable through the port of the tube and slidable within the lumen.

18. The system of claim 17, wherein the delivery member further comprises a grip handle attached to and extending proximally from the circular element.

19. The system of claim 17, wherein the tube further comprises a valve disposed within the lumen structured to reduce backflow of blood out of the heart after the tube has passed through the apical area of the heart.

* * * * *